United States Patent [19]

Goto et al.

[11] Patent Number: 4,748,154

[45] Date of Patent: May 31, 1988

[54] PEPTIDE DERIVATIVES, THEIR PRODUCTION AND USE

[75] Inventors: Giichi Goto, Toyono; Akinobu Nagaoka, Kawanishi; Mitsuhiro Wakimasu, Suita, all of Japan

[73] Assignee: Takeda Chemical Industries, Ltd., Osaka, Japan

[21] Appl. No.: 939,103

[22] Filed: Dec. 8, 1986

[30] Foreign Application Priority Data

Dec. 24, 1985 [JP] Japan ................... 60-291474

[51] Int. Cl.$^4$ .................... A61K 37/02; C07K 7/06
[52] U.S. Cl. ................................ 514/16; 530/329
[58] Field of Search ............... 530/330, 329; 514/16

[56] References Cited

U.S. PATENT DOCUMENTS 4,487,765 12/1984 de Wied ........................ 530/329
4,623,640 11/1986 de Wied ........................ 530/330

FOREIGN PATENT DOCUMENTS 161017 11/1985 European Pat. Off. .

OTHER PUBLICATIONS

Science, 221 (1983), 1310–1312.

Primary Examiner—Delbert R. Phillips
Attorney, Agent, or Firm—Wenderoth, Lind & Ponack

[57] ABSTRACT

A peptide derivative of the general formula

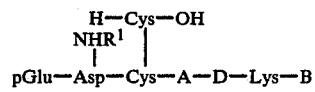

wherein
$R^1$ is a hydrogen atom, a $C_{1-18}$ alkyl group or a substituted or unsubstituted phenyl $C_{1-3}$ alkyl group;
A is an amino or N—$C_{1-6}$ alkylamino acid residue;
B is a hydroxyl group, a substituted or unsubstituted amino group, or an amino acid or an amide thereof, or a physiologically acceptable salt thereof, can be advantageously used for the treatment and/or prevention of a disease including, among others, senile dementia (Alzheimer's dementia), cerebrovascular dementia, Alzheimer's disease, Pick's disease, Huntington's chorea, Creutzfeldt-Jakob disease, Parkinson's disease, and dementia due to spinocerebellar degeneration.

12 Claims, No Drawings

PEPTIDE DERIVATIVES, THEIR PRODUCTION AND USE

The present invention relates to a vasopressin fragment peptide derivative having nootropic activity and, therefore, of value as a drug.

It is known for years that vasopressin has nootropic activity [Int. J. Neuropharmacol. 4, 157–167(1965)]. Recently, it has been reported that certain peptides which may be regarded as fragments of vasopressin, e.g.

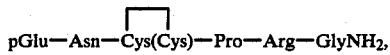

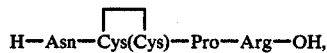

etc., also have nootropic activity [Science 221, 1310–1312(1983); Dutch patent application No. 82/03949, No. 82/04881, and No. 84/01187]

The present inventors studied to obtain compounds having nootropic activity surpassing that of said vasopressin fragment peptides and found that certain [D-Lys]-derivatives have nootropic activity. The present invention has been accomplished on the basis of the above finding and further research.

The present invention relates to:

(1) A peptide derivative of the general formula;

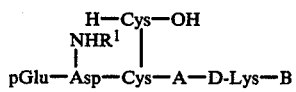

wherein
$R^1$ is a hydrogen atom, an alkyl group or a substituted or unsubstituted phenylalkyl group;
A is an amino or N-alkylamino acid residue;
B is a hydroxyl group, a substituted or unsubstituted amino group, or an amino acid or an amide thereof, (2) A method of producing the same derivative (I) and (3) A pharmaceutical composition characteristically featured by containing the same derivative (I).

Throughout this specification, amino acids and peptides are referred to by the abbreviations which are either used routinely in the art or have been adopted by the nomenclature committee of IUPAC-IUB. For example, the following abbreviations are used. It should also be understood that unless otherwise indicated, the chirality is natural form, i.e. L configuration.

Ala: Alanine
Asp: Aspartic acid
Asn: Asparagine
Cys: Cysteine
Gly: Glycine
Sar: Sarcosine
Leu: Leucine
Ile: Isoleucine
Phe: Phenylalanine
Pro: Proline
Lys: Lysine
pGlu: Pyroglutamic acid
MeAla: N-Methylalanine
Azc: Azetidine-2-carboxylic acid
Pip: Pipecolinic acid Further, the compounds referred to often in this specification are disignated by the following abbreviations.
DCC: N,N'-Dicyclohexylcarbodiimide
DCU: N,N'-Dicyclohexylurea
HONB: N-Hydroxy-5-norbornene-2,3-dicarboximide
ONB: HONB ester
HOBt: 1-Hydroxybenzotriazole
HOSu: N-Hydroxysuccinimide
OSu: HOSu ester
Z: Benzyloxycarbonyl
Boc: t-Butoxycarbonyl
MBzl: p-Methoxybenzyl
Bzl: Benzyl
ada: Adamantyl
$Bu^t$: t-Butyl
Et: Ethyl
p-Tos-OH: P-Toluenesulfonic acid
TFA: Trifluoroacetic acid
HF: Hydrogen fluoride
MSA: Methanesulfonic acid
TEA: Triethylamine
DCHA: Dicyclohexylamine
MeOH: Methanol
AcOH: Acetic acid
AcOEt: Ethyl acetate
DMF: N,N,-dimethylformamide Referring to the above-mentioned general formula (I) and prticularly to $R^1$ which represents a hydrogen atom, an alkyl group or a substituted or unsubstituted phenylalkyl group, the alkyl group is a straight-chain or branched alkyl group of 1 to 18 carbon atoms, such as methyl, ethyl, n-propyl, isopropyl, n-butyl, sec-butyl, t-butyl, n-pentyl, cyclopentyl, n-hexyl, cyclohexyl, n-heptyl, cycloheptyl, n-octyl, n-nonyl, n-decyl, stearyl, adamantyl and so on. The substituted or unsubstituted phenylalkyl group may for example be phenylmethyl, phenylethyl, phenylpropyl or the like. The substituents may for example be nitro, halogen (for example, fluorine, chlorine, bromine and iodine), lower alkoxy ($C_{1-3}$ alkoxy; for example, methoxy, ethoxy, propoxy, isopropoxy) and so on. Any desired number of such substituents may be present in optional positions on the benzene ring.

Referring, further, to the general formula (I) and particularly to the amino acid or N-alkylamino acid residue represented by A, the amino acid is not particularly limited in kind but is preferably an amino acid or N-alkylamino acid residue of the formula

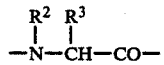

wherein $R^2$ and $R^3$ may be the same or different and each means a hydrogen atom or a substituted or unsubstituted alkyl group, or $R^2$ and $R^3$ may join together to form a ring of $-(CH_2)_n-$ (wherein n is an integer of 2 to 4). This amino acid may be whichever of the D-form and the L-form.

The substituted or unsubstituted lower alkyl group is a straight-chain or branched alkyl group of 1 to 6 carbon atoms, such as methyl, ethyl, n-propyl, isopropyl, n-butyl, sec-butyl, t-butyl, n-pentyl, cyclopentyl, neopentyl, n-hexyl, cyclohexyl, etc. The substituents may be $-NH_2$, $-COOH$, $-CONH_2$, $-OH$ and so on. The number of substituents is generally about 1 to 2. Specific examples of said amino acid or N-alkylamino acid residue include Pro, Gly, Ala, Sar, MeAla, Azc, Pip and so on.

When B in the general formula (I) represents a hydroxyl group, this terminal of the peptide is D—Lys—OH, that is —COOH derived from D—Lys.

The substituted or unsubstituted amino group for B means a group of the formula —NHR$^4$ (wherein R$^4$ is a hydrogen atom or an alkyl group). This alkyl group may be a straight-chain or branched alkyl group of 1 to 10 carbon atoms, such as methyl, ethyl, n-propyl, isopropyl, n-butyl, sec-butyl, t-butyl, n-pentyl, cyclopentyl, neopentyl, n-hexyl, cyclohexyl, n-heptyl, cycloheptyl, n-octyl, n-nonyl, n-decyl, adamantyl and so on.

When B is an amino acid or an amide thereof, the amino acid is not particularly limited in kind but preferably is an amino acid of the formula

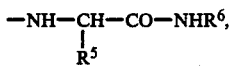

(wherein R$^5$ is a hydrogen atom, an alkyl group or a phenylalkyl group and R$^6$ is a hydrogen atom or an alkyl group). This amino acid may be whichever of the D-form and the L-form.

When R$^5$ and R$^6$ are alkyl groups, they may be straight-chain or branched alkyl groups such as methyl, ethyl, n-propyl, isopropyl, n-butyl, sec-butyl, t-butyl, n-pentyl, cyclopentyl, neopentyl, n-hexyl, cyclohexyl and so on.

The phenylalkyl group R$^5$ may be any of the substituted or unsubstituted phenylalkyl groups mentioned hereinbefore for R$^1$.

As examples of the amino acid or amide thereof represented by B, there may be mentioned Gly, Ala, Leu, Ile, Phe, Gly—NHR$^6$, Ala—NHR$^6$ and Leu—NHR$^6$ (wherein R$^6$ has the same meaning as defined hereinbefore).

The objective compound (I) of the present invention can be synthesized by the known technology in the art of peptide synthesis. However, in a preferred method, a compound of the general formula

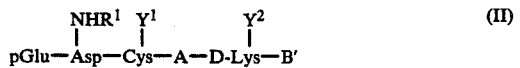

[R$^1$ and A are as defined in connection with the general formula (I); B' is a protected hydroxyl group, a protected amino group which may be substituted or unsubstituted, or a protected amino acid or an amide thereof; Y$^1$ and Y$^2$ each is a protective group] is first prepared and, after a deprotection reaction, the resulting cysteine-containing peptide is reacted with cysteine or cystine monosulfoxide.

Referring to the above-mentioned general formula (II), the protective group Y$^1$ is exemplified by p-methoxybenzyl, benzyl, t-butyl, adamantyl, trityl, acetamidomethyl, carbomethoxysulfenyl, 3-nitro-2-pyridinesulfenyl and so on.

The protective group Y$^2$ is exemplified by benzyloxycarbonyl, t-butoxycarbonyl, t-amyloxycarbonyl, isobornyloxycarbonyl, chloro- or nitro-substituted benzyloxycarbonyl, p-methoxybenzyloxycarbonyl, trityl, diphenylphosphinothioyl, 2,3,6-trimethylbenzenesulfonyl and so on.

The protective group for the carboxyl group in B' may for example be benzyl, t-butyl or the like.

To synthesize a peptide derivative having the chemical structure of general formula (II), an amino acid compound or peptide capable of constituting a portion of the polypeptide (II) is condensed with a compound capable of constituting the remaining portion by a method for peptide synthesis. This method may be any of the known methods, among which are the methods described in M. Bodansky and M. A. Ondetti: Peptide Synthesis, Interscience, New York, 1966; F. M. Finn and K. Hofmann: The Proteins, vol. 2, H. Nenrath and R. L. Hill (ed.), Academic Press, Inc., New York, 1976; and Nobuo Izumiya et al: Foundamentals and Experiments of Peptide Synthesis, Maruzen, 1985, for instance. Thus, the azide method, chloride method, acid anhydride method, mixed acid anhydride method, DCC method, active ester method, Woodward's reagent k method, carbodiimidazole method, redox method, DCC/HONB method, and so on may be mentioned by way of example. Depending on cases, the NCA method (the N-carboxyanhydride method in which, instead of using a protective group, an intramolecular cyclic carbonyl compound corresponding to the amino acid is employed may also be applicable.

Prior to the condensation reaction, the carboxyl and amino groups of starting materials which are not to take part in the reaction may be protected and/or the carboxyl and amino groups that are to take part in the reaction may be activated, by the procedures known per se in each case.

As the protective groups for the starting materials, those mentioned hereinbefore can be used. The carboxyl groups in the starting materials can also be protected in the form of metal salts (e.g. sodium salt, potassium salt, etc.), t-alkylamine salts (e.g. triethylamine salt, N-methylmorpholine salt, etc.) or esters (e.g. methyl, ethyl, benzyl, p-nitrobenzyl, t-butyl, t-amyl and other esters). As protective groups for the amino groups of starting materials, there may be mentioned such groups as benzyloxycarbonyl, t-butoxycarbonyl, isobornyloxycarbonyl, 9-fluorenylmethyloxycarbonyl and so on.

As the activated forms of carboxyl groups in the starting materials, there may be mentioned the corresponding acid anhydrides, azides and activated esters such as esters of alcohols (e.g. pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide, N-hydroxybenzotriazole, etc.), for instance. The activated forms of amino groups in starting materials include the corresponding phosphoric acid amides.

The starting materials being represented by P$^1$ and P$^2$ for the convenience of explanation, the possible exemplary combinations of the above-mentioned forms of carboxyl and amino groups in P$^1$-P$^2$ are shown in the following table.

| Examples of combination | Starting materials | | | |
| --- | --- | --- | --- | --- |
| | P$^1$ | | P$^2$ | |
| | COOH | NH$_2$ | COOH | NH$_2$ |
| 1* | Free | Protected | Protected | Free |
| 2 | Activated | Protected | Free | Free |
| 3 | Free | Protected | Protected | Activated |

Note:
In the case of *, a carbodiimide (e.g. N,N'—dicyclohexylcarbodiimide) is preferably present as a dehydrating agent in the reaction system.

The condensation reaction may be conducted in the presence of a solvent. The solvent is selected from among those which are known to be useful for peptide condensation reactions. For example, there may be mentioned dimethylformamide, dimethyl sulfoxide, pyridine, chloroform, dioxane, dichloromethane, tetrahydrofuran, acetonitrile, etc. and suitable mixtures thereof, either in anhydrous state or in water-containing condition.

The reaction temperature is selected from the temperature range which is known to be applicable to peptide forming reactions, and generally is within the range of about $-20°$ C. to about $30°$ C. Precursors (protected peptides) of the compound according to the present invention can be easily prepared by solid phase synthesis, too.

The protected compound of general formula (II) thus prepared is subjected to deprotection reaction. This reaction varies with different protective groups used. In any event, however, it is commercially advantageous that all the protective groups be eliminated in one step without interferring with the peptide bonds. Therefore, selection of protective groups is done taking the above into consideration. In the case of cysteine-containing peptides, however, there are cases in which, from the standpoint of the ease of purification, one preferably uses a two-step elimination procedure, i.e. removes the protective groups other than the thiol-protecting group in the first step and, then, removes the thiol-protecting group in the second step. As examples of the thiol-protecting group that can be used in such cases, there may be mentioned acetamidomethyl, 3-nitro-2-pyridinesulfenyl and so on.

As exemplary methods for removing the protective groups, there may be mentioned acid treatment using anhydrous hydrogen fluoride, methanesulfonic acid, trifluoromethanesulfonic acid, trifluoroacetic acid or the like, or a mixture thereof, and reduction with sodium metal in liquid ammonia. Deprotection by the above-mentioned acid treatment is generally carried out at an appropriate temperature within the range of $-20°$ C. to $40°$ C., and in this procedure, a cation acceptor such as anisole, phenol, thioanisole, dimethyl sulfide or the like is preferably added. Moreover, when the thiol-protecting groups are refractory to acid treatment, such as acetamidomethyl and 3-nitro-2-pyridinesulfenyl, the former can be eliminated with iodine and mercury acetate and the latter with mercaptoethanol, for instance.

For the introduction of cysteine into the thiol peptide thus obtained upon deprotection of the protected peptide (II), there may be employed the method in which the thiol peptide and cysteine are subjected to oxidation reaction in a solvent such as water by means of an oxidizing agent such as air, iodine, diiodoethane, potassium ferricyanide, or the like. However, depending on cases, the above known method may give rise to byproducts such as cystine and peptide dimer in addition to the objective compound (I), thus causing a decrease in product yield. The present inventors investigated other possible methods for introducing cysteine and found that the objective compound (I) can be obtained in good yield by using cystine monosulfoxide [described in J. Chem. Soc. (C). 1971, p. 2326]. Generally, this reaction is conducted in an aqueous solution at an appropriate temperature within the range of $0°$ C. to $40°$ C. Thus, by mixing about ½ equivalent of cystine monosulfoxide with the thiol peptide, this reaction is completed within a few minutes to give the objective compound (I) without formation of byproducts.

Following the above reaction, the peptide derivative (I) so produced is isolated by the peptide separation procedures such as extraction, redistribution, reprecipitation, recrystallization, column chromatography and so on.

The peptide derivative (I) according to the present invention can be provided in the form of an acid addition salt, especially a physiologically acceptable acid addition salt, such as salts with inorganic acids (e.g. hydrochloric acid, sulfuric acid, phosphoric acid, etc.) or organic acids (e.g. acetic acid, propionic acid, citric tartaric acid, malic acid, oxalic acid, methanesulfonic acid, etc.).

The peptide derivative (I) and salt according to the present invention exhibit strong nootropic activity in a passive avoidance test in mice and this activity is higher than that of vasopressin and other known neuropeptides.

The diseases in which the peptide derivative (I) and salt according to the present invention can be advantageously indicated include senile dementia (Alzheimer's dementia), cerebrovascular dementia, Alzheimer's disease, Pick's disease, Huntington's chorea, Creutzfeldt-Jakob disease, Parkinson's disease, and dementia due to spinocerebellar degeneration, for instance, and these compounds can be used for the prevention or treatment of such diseases in mammals (e.g. monkey, human).

The toxicity of the peptide derivative (I) and salt according to the present invention is very low and they cause no death even at the dose of 100 mg/kg which is far beyond the effective dose.

The peptide derivative according to the present invention can be administered in the free form or as an acid addition salt. For both the free from and acid addition salt of derivative (I), the dosage is preferably in the range of 1 ng to 1 mg per kg body weight in terms of the free compound. The derivative according to the present invention is mainly administered non-orally (for example, by the intraventricular or intraspinal route, nasal route, or rectal route) but in certain cases may be administered orally.

The useful dosage forms include injections, suppositories, powders, pills, tablets and so on. As the derivative according to the present invention is a stable substance, it can be stored as dissolved in physiological saline but may be prepared into a lyophilized ampule preparation with the addition of mannitol, sorbitol or the like and extemporaneously reconstituted.

The following are the results of pharmacological test example indicating the effectiveness of compounds (I) of the present invention.

PHARMACOLOGICAL TEST EXAMPLE

The effect on memory process was tested in a one-trial passive avoidance task in C57BL/6 mice. The learning procedure was fundamentally the same as that used by Burbach et al (Science; 221, 1310–1312, 1983). The apparatus consisted of an illuminated compartment attached to a dark one with grid floor. Mice were placed in the light compartment and allowed to enter the dark one. When mice entered the dark compartment, an electric footshock (0.4 mA, 3 sec) was delivered. Immediately after receiving a footshock, mice were administered with cycloheximide (20 mg/kg, sc), a protein synthesis inhibitor, and a retention test trial was carried out 24 hours later. Retention of passive avoidance behavior was measured by the latency to reenter the dark compartment after placing mice in the light compartment. Five minutes before the testing, mice were treated with 5 μl of peptide in a dose of 10 pg and 10 ng by intracerebroventricular injection through a hypodermic needle attached to a 25 μl syringe. Compounds of the present invention were dissolved in saline. Control mice injected with saline typically showed short latencies within 20 sec, which indicated retrograde amnesia. Median latencies in peptide-treated groups were expressed as a percentage of that in control, and either Mann-Whitney U test for latencies or chi-square test for percent of mice showing latencies longer than 50 seconds was used in statistical analysis. Number of mice used in each group was 9–22.

An active metabolite of arginine vasopressin

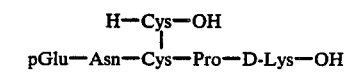

in the brain (de Wied et al; Pharmacol. Biochem. Behav., 21, 393–400, 1984) significantly prolonged the latency to 191% of control in a dose of 10 pg (U(15,16)=60, P<0.05). The compounds of Example 1 and Example 15 reversed amnesia significantly, as demonstrated by longer latencies of 238% (x2=6.18, P<0.05) and 200% (U(9,19)=20, P<0.05), respectively. The compounds of Example 6 and Example 8 also reversed amnesia; the latency was 238% (U(10,10)=26) and 179% (U(10,10)=27), respectively, (P<0.1).

These results demonstrate that compounds of the present invention have central action of improving memory impairment induced by cycloheximide in mice.

The present invention will be described in further detail by way of examples. In the purification of final products, Sephadex G-25 and LH20 (Pharmacia, Sweden) were used. The purity of the compounds produced was tested by thin layer chromatography on KieselGel 60F-254 (Merck, Germany). The developing solvent systems used are as follows.

$Rf^1$: Chloroform-methanol-acetic acid (9:1:0.5)
$Rf^2$: Chloroform-methanol (19:1)
$Rf^3$: Chloroform-methanol-acetic acid-water (32:8:1:1)
$Rf^4$: Ethyl acetate-n-butanol-acetic acid-water (1:1:1:1)
$Rf^5$: Chloroform-acetone-methanol (10:3:2).

REFERENCE EXAMPLE

Production of cystine monosulfoxide

Cystine monosulfoxide was prepared in accordance with the method described in J. Chem. Soc. (c), 1971, 2326.

In 44 ml of 2N sulfuric acid was dissolved 4.81 g of cystine and after ice-cooling, $CH_3COOH$ (a solution prepared by reacting 5.5 ml of 30% hydrogen peroxide with 25 ml of acetic anhydride at 40° C. for 12 hours) was added dropwise. The mixture was further stirred at 4° C. or less for 15 hours, at the end of which time it was adjusted to pH 4 with pyridine. To this solution was added 240 ml of ethanol and the resulting crystals were collected by filtration. The crystals were dissolved in 1 l of 0.5N AcOH and after removal of insoluble matter, 1.5 l of acetone was added. The crystals formed were harvested by filtration and washed with methanol and ether in that order.

Yield: 2.68 g (52.2%).

m.p.: 191°–193° C. (decompn.).
$[\alpha]_D^{23}+46.1°$ (c=1.0, 1N—$H_2SO_4$).

Elemental analysis, for $C_6H_{12}N_2O_5S_2$: Calcd. C, 28.12; H, 4.72; N, 10.93; S, 25.02. Found C, 27.82; H, 4.47; N, 10.81; S, 25.16.

EXAMPLE 1

Production of

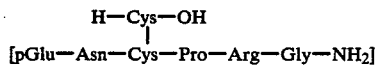

(I)

Preparation of Boc—D—Lys(Z)—OBzl

In 50 ml of AcOEt was suspended 3.37 g of Boc—D—Lys(Z)—OH.DCHA, followed by addition of 20 ml of water and 9 ml of 1N-sulfuric acid. The mixture was shaken, washed with water, and dried over anhydrous sodium sulfate. After the desiccant was filtered off, 0.83 ml of benzyl bromide and 1.0 ml of TEA were added to the filtrate, and the mixture was refluxed for 15 hours. The reaction mixture was washed with water, dried over anhydrous sodium sulfate and concentrated. To the concentrate was added petroleum ether and the resulting crystals were collected by filtration.

Yield: 2.6 g.
m.p.: 54°–56° C.
$Rf^1$: 0.87.
$[\alpha]_D^{24}+21.3°$ (c=1.1, MeOH).

Elemental analysis, for $C_{26}H_{34}N_2O_6$: Calcd. C, 66.36; H, 7.28; N, 5.95. Found C, 66.59; H, 7.27; N, 5.95.

(II)

Preparation of Boc—Cys(MBzl)—Pro—OH.DCHA

In 150 ml of acetonitrile were dissolved 14.0 g of Boc—Cys(MBzl)—OH and 8.1 g of HONB, and after ice-cooling, 9.3 g of DCC was added. The mixture was stirred for 15 hours, after which DCU was filtered off. Separately, 5.18 g of Pro and 3.44 g of sodium hydrogen carbonate were dissolved in 50 ml of water, followed by addition of 50 ml of acetonitrile and 30 ml of DMF. While this mixture was stirred vigorously, the acetonitrile solution of Boc—Cys(MBzl)—ONB prepared above was added. The mixture was stirred for 8 hours. The reaction mixture was then concentrated, acidified with 10% aqueous citric acid, and extracted with 300 ml of AcOEt. The extract was washed with water and dried over anhydrous sodium sulfate. It was further concentrated and the residue was dissolved in 200 ml of ether. To this solution was added 8.2 ml of DCHA and the resulting crystals were collected by filtration and recrystallized from methanol-ether.

Yield: 18.6 g (73.2%).
m.p.: 162°–163° C.
$Rf^1$: 0.69.
$[\alpha]_D^{24}-39.6°$ (c=0.9, MeOH).

Elemental analysis, for $C_{33}H_{53}N_3O_6S$: Calcd. C, 63.94; H, 8.62; N, 6.78; S, 5.17. Found C, 64.09; H, 8.59; N, 6.83; S, 5.09.

(III)

Preparation of
Boc—Asn—Cys(MBzl)—Pro—OH.DCHA

In 250 ml of AcOEt was suspended 18.0 g of Boc—Cys(MBzl)—Pro—OH.DCHA, followed by addition of 100 ml of water and 35 ml of 1N-sulfuric acid. After shaking, the mixture was dried over anhydrous sodium sulfate and concentrated. The concentrate was dissolved in 80 ml of TFA-water (19:1) with shaking and the solution was concentrated and precipitated with ether. The precipitate was collected by filtration and dried. Separately, 6.73 g of Boc—Asn—OH and 5.34 g of HONB were dissolved in 50 ml of DMF and under ice-cooling, 6.60 g of DCC was added. The mixture was stirred under ice-cooling for 8 hours, at the end of which time DCU was filtered off. The amine component prepared previously was dissolved in 50 ml of DMF, followed by addition of 8.4 ml of TEA. Then, the DMF solution of Boc—Asn—ONB was added thereto and stirred for 15 hours. The reaction mixture was concentrated, acidified with 10% citric acid and extracted with AcOEt. The extract was washed with water, dried over anhydrous sodium sulfate, and concentrated. The concentrate was dissolved in 50 ml of methanol, and after addition of 5 ml of DCHA, the solution was concentrated. To the residue was added AcOEt and after cooling, the crystals were collected by filtration and washed with AcOEt.

Yield: 14.8 g (69.5%).
m.p.: 142°–143° C.
$Rf^1$: 0.49.
$[\alpha]_D^{24} - 58.3°$ (c=1.0, MeOH).

Elemental analysis, for $C_{37}H_{59}N_5O_8S$: Calcd. C, 60.55; H, 8.10; N, 9.54; S, 4.37. Found C, 60.90; H, 8.22; N, 9.31; S, 4.20.

(IV)

Preparation of pGlu—Asn—Cys(MBzl)—Pro—OH

In 200 ml of AcOEt was suspended 6.5 g of Boc—Asn—Cys(MBzl)—Pro—OH.DCHA, followed by addition of 50 ml of water and 11 ml of 1N-sulfuric acid. After shaking, the mixture was washed with water, dried over anhydrous sodium sulfate and concentrated. The residue was dissolved in 40 ml of TFA-water (19:1) with shaking and concentrated again. To the concentrate was added ether and the precipitate was recovered by filtration and dried. This was dissolved in 50 ml of DMF and under ice-cooling, 2.9 ml of TEA and, then, 2.6 g of pGlu—ONB were added. The mixture was stirred for 15 hours. The reaction mixture was concentrated and 3 ml of AcOH was added. The mixture was stirred well and further stirred with the addition of ether. The ether was decanted off, AcOEt was added, and the resulting precipitate was collected by filtration and reprecipitated from MeOH—AcOEt.

Yield: 4.65 g (93.0%).
m.p.: 126°–129° C.
$Rf^1$: 0.15.
$[\alpha]_D^{24} - 94.7°$ (c=1.2, MeOH).

Elemental analysis, for $C_{25}H_{33}N_5O_8S \cdot H_2O$: Calcd. C, 51.62; H, 6.07; N, 12.04; S, 5.51. Found C, 51.91; H, 6.00; N, 12.03; S, 5.45.

(V)

Preparation of
pGlu—Asn—Cys(MBzl)—Pro—D—Lys(Z)—OBzl

In 10 ml of TFA was dissolved 0.62 g of Boc—D—Lys(Z)—OBzl with stirring and the solution was concentrated. To the concentrate was added an aqueous solution of NaHCO$_3$, and the mixture was extrated with AcOEt and dried over anhydrous sodium sulfate. After concentration, the residue was dissolved in 5 ml of DMF, followed by addition of 0.56 g of pGlu—Asn—Cys(MBzl)—Pro—OH and 0.15 g of HOBt. Then, under ice-cooling, 0.15 g of DCC was added and the mixture was stirred for 15 hours. The DCU was filtered off, the filtrate was concentrated, and AcOEt was added to the concentrate. The resulting gel was collected by filtration and reprecipitated from MeOH—AcOEt.

Yield: 0.74 g (80.8%).
m.p.: 150°–152° C.
$Rf^1$: 0.46.
$[\alpha]_D^{24} - 32.1°$ (c=1.3, DMF).

Elemental analysis, for $C_{46}H_{57}N_7O_{11}S$: Calcd. C, 60.31; H, 6.27; N, 10.70; S, 3.50. Found C, 60.15; H, 6.38; N, 10.57; S, 3.72.

(VI)

Preparation of

pGlu—Asn—Cys—Pro—D-Lys—OH

In 5 ml of HF was dissolved 0.60 g of pGlu—Asn—Cys(MBzl)—Pro—D—Lys(Z)—OBzl in the presence of 0.5 ml of anisole, and the solution was stirred at 0° C. for 1 hour. The solution was then concentrated and precipitated with ether and the ether was removed by decantation. The residue was dissolved in water, passed through an Amberlite IRA-400 (acetate form) column (1×10 cm), and lyophilized. The lyophilizate was dissolved in 2 ml of 1N-AcOH and applied to a Sephadex LH20 column (2.2×123 cm). Elution was carried out with 1N-acetic acid. The fractions from 200 to 235 ml were pooled and lyophilized. Yield 310 mg (83%). A 120 mg portion of the above product was dissolved in 2 ml of water followed by addition of 30 mg of cystine monosulfoxide. The mixture was stirred at room temperature for 30 minutes and, then, applied to a Sephadex LH20 column (2.2×123 cm). Elution was carried out with 1N-acetic acid and the fractions from 173 to 194 ml were combined and lyophilized.

Yield: 107 mg (63%).
$Rf^4$: 0.07.
$[\alpha]_D^{23} - 151.7°$ (c=0.4, 1N-AcOH).

Amino acid analysis: Lys 1.00; Asp 1.03; Glu 1.05; Pro 0.95; Half Cys 1.67.

EXAMPLE 2

Production of

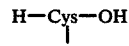
pGlu—Asn—Cys—Pro—D-Lys—NH$_2$

(I)

Preparation of Boc—D—Lys(Z)—NH₂

In 50 ml of AcOEt was suspended 2.0 g of Boc—D—Lys(Z)—OH.DCHA, followed by addition of 20 ml of water and 5 ml of 1N-sulfuric acid. The mixture was shaken, washed with water, dried over anhydrous sodium sulfate and concentrated. The concentrate was dissolved in 20 ml of acetonitrile and after ice-cooling, 0.71 g of HONB, 0.81 g of DCC and 0.5 ml of an aqueous solution of C—NH₃ were added. The mixture was stirred for 15 hours, at the end of which time the insoluble matter was filtered off. The filtrate was concentrated and the residue was dissolved in AcOEt, washed with aqueous NaHCO₃, dried over anhydrous sodium sulfate, and concentrated. To the concentrate was added ether and the resulting crystals were harvested by filtration.

Yield: 1.3 g (96.2%).
m.p.: 139°–140° C.
Rf¹: 0.70.
$[\alpha]_D^{24}$ −1.3° (c=0.9, MeOH).
Elemental analysis, for $C_{19}H_{29}N_3O_5$: Calcd. C, 60.14; H, 7.70; N, 11.07. Found C, 60.63; H, 7.95; N, 11.22.

(II)

Preparation of pGlu—Asn-Cys(MBzl)—Pro—D—Lys(Z)—NH₂

In 8 ml of TFA was dissolved 0.81 g of Boc—D—Lys(Z)—NH₂ with shaking and after concentration, ether was added. The resulting precipitate was collected by filtration. The precipitate was dissolved in 10 ml of DMF and under ice-cooling, 0.4 ml of TEA and 1.0 g of pGlu—Asn—Cys(MBzl)—Pro—ONB (prepared from 1.0 g of pGlu—Asn—Cys(MBxl)—Pro—OH, 0.36 g of HONB and 0.41 g of DCC) were added. The mixture was stirred for 15 hours, after which DCU was filtered off. The filtrate was concentrated, water was added to the residue, and the resulting precipitate was collected by filtration. The precipitate was suspended in acetonitrile, heated and, then, cooled, and the resulting gel was recovered by filtration.

Yield: 1.14 g (66.2%).
m.p.: 155°–158° C.
Rf¹: 0.19.
$[\alpha]_D^{24}$ −26.6° (c=0.9, DMF).
Elemental analysis, for $C_{39}H_{52}N_8O_{10}S$: Calcd. C, 56.78; H, 6.35; N, 13.58; S, 3.89. Found C, 56.59; H, 6.67; N, 13.29; S, 3.70.

(III)

Preparation of

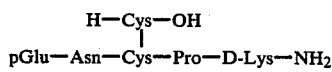

To 0.80 g of pGlu—Asn—Cys(MBzl)—Pro—D—Lys(Z)—NH₂ were added 5 ml of MSA and 1.3 ml of anisole and the mixture was shaken at room temperature for 1 hour. The reaction mixture was precipitated with ether, the ether was decanted off, and the residue was passed through an Amberlite IRA-400 (acetate form) column (3×5 cm). To the eluate was added 124 mg of cystine monosulfoxide and the mixture was shaken at room temperature for 30 minutes and lyophilized. The lyophilizate was dissolved in 2 ml of 1N-AcOH and applied to a Sephadex G-25 column (2.6×126 cm). Elution was carried out with 1N-acetic acid and the fractions corresponding to 380 to 465 ml were combined and lyophilized.

Yield: 440 mg (60%).
Rf⁴: 0.07.
$[\alpha]_D^{23}$ −143.4° (c=0.4, 1N-AcOH).
Amino acid analysis: Lys 1.00; Asp 1.02; Glu 1.10; Pro 1.03; Half Cys 1.71.

EXAMPLE 3

Production of

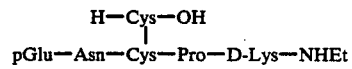

(I)

Preparation of Boc—D—Lys(Z)—NH—Et

In 200 ml of AcOEt was suspended 4.22 g of Boc—D—Lys(Z)—OH.DCHA, followed by addition of 50 ml of water and 10 ml of 1N-sulfuric acid. After shaking, the solution was dried over anhydrous sodium sulfate and concentrated. The concentrate was dissolved in 40 ml of acetonitrile followed by addition of 1.49 g of HOBt.NH₂—Et. Under ice-cooling, 1.56 g of DCC was added and the mixture was stirred for 15 hours. Then, DCU was filtered off, the filtrate was concentrated, and the concentrate was dissolved in AcOEt. This solution was washed with 0.5N-HCl and aqueous NaHCO₃ in that order, dried over anhydrous sodium sulfate, and concentrated. To the concentrate was added petroleum ether and the resulting precipitate was collected by filtration.

Yield: 2.70 g (88.2%).
m.p.: 102°–104° C.
Rf²: 0.45.
$[\alpha]_D^{24}$ +6.2° (c=1.4, MeOH).
Elemental analysis, for $C_{21}H_{33}N_3O_5$: Calcd. C, 61.90; H, 8.16; N, 10.31. Found C, 62.24; H, 8.31; N, 10.30.

(II)

Preparation of pGlu—Asn—Cys(MBzl)—Pro—D—Lys(Z)—NH—Et

In the same manner as Example 2-(II), the above-idenified compound was prepared using 1.23 g of Boc—D—Lys(Z)—NHEt, 1.69 g of pGlu—Asn—Cys(MBzl)—Pro—OH, 1.07 g of HONB, and 0.93 g of DCC. The product was reprecipitated from acetonitrile-AcOEt.

Yield: 1.45 g (56.7%).
m.p.: 175°–180° C.
Rf³: 0.42.
$[\alpha]_D^{24}$ −36.8° (c=0.7, MeOH).
Elemental analysis, for $C_{41}H_{56}N_8O_{10}S.H_2O$: Calcd. C, 56.53; H, 6.71; N, 12.87; S, 3.68. Found C, 56.58; H, 6.83; N, 12.16; S, 2.98.

(III)

Preparation of

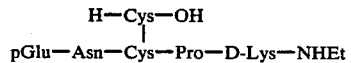

In the same manner as Example 2-(III), 0.80 g of pGlu—Asn—Cys(MBzl)—Pro—D—Lys(Z)—NHEt was treated with MSA-anisole, reacted with 117 mg of cystine monosulfoxide and purified on a Sephadex G-25 column to give the above-identified compound.

Yield: 400 mg (56.0%).
Rf⁴: 0.14.
Amino acid analysis: Lys 1.00; Asp 0.98; Glu 1.05; Pro 1.03; Half Cys 1.69; EtNH₂ 0.95.

EXAMPLE 4

Production of

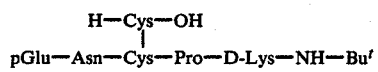

(I)

Preparation of Boc—D—Lys(Z)—NH—Buᵗ

In the same manner as Example 3-(I), the above-identified compound was prepared as an oil using 0.70 g of Boc—D—Lys(Z)—OH.DCHA, 0.31 g of HOBt.N-H₂—Buᵗ and 0.31 g of DCC.

Yield: 0.54 g (quantitative).
Rf¹: 0.74.

(II)

Preparation of pGlu—Asn—Cys(MBzl)—Pro—D—Lys(Z)—NHBuᵗ

The above compound was prepared in the same manner as Example 1-(V) using 0.50 g of Boc—D—Lys(Z)—NH—Buᵗ, 0.56 g of pGlu—Asn—Cys(MBzl)—Pro—OH, 0.15 g of HOBt and 0.23 g of DCC.

Yield: 0.65 g (73.2%).
m.p.: 147°–149° C.
Rf¹: 0.37.
$[\alpha]_D^{24}$ −25.2° (c=0.4, DMF).
Elemental analysis, for $C_{43}H_{60}N_8O_{10}S \cdot H_2O$: Calcd. C, 57.44; H, 6.95; N, 12.46; S, 3.57. Found C, 57.68; H, 7.12; N, 12.08; S, 3.23.

(III)

Preparation of

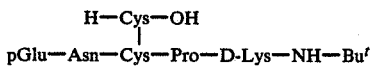

In the same manner as Example 2-(III), 0.60 g of pGlu—Asn—Cys(MBzl)—Pro—D—Lys(Z)—N-H—Buᵗ was treated with MSA-anisole, reacted with 88 mg of cystine monosulfoxide, and purified on a Sephadex G-25 column to give the above-identified compound.

Yield: 290 mg (53%).
Rf⁴: 0.17.
$[\alpha]_D^{23}$ −142.4° (c=0.4, 1N-AcOH).
Amino acid analysis: Lys 1.00; Asp 0.99; Glu 1.07; Pro 1.05; Half Cys 1.73.

EXAMPLE 5

Production of

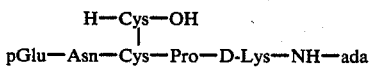

(I)

Preparation of Boc—D—Lys(Z)—NH—ada

Using 0.70 g of Boc—D—Lys(Z)—OH.DCHA, 0.34 g of adamantylamine hydrochloride, 0.20 g of HOBt, 0.31 g of DCC and 0.25 ml of TEA, the procedure of Example 3-(I) was repeated to obtain the above-identified compound as an oil.

Yield: 0.65 g (quantitative).
Rf¹: 0.79.

(II)

Preparation of pGlu—Asn—Cys(MBzl)—Pro—D—Lys(Z)—N-H—ada

In the same manner as Example 1-(IV), the above-identified compound was prepared using 0.65 g of Boc—D—Lys(Z)—NH—ada, 0.56 g of pGlu—Asn—Cys(MBzl)—Pro—OH, 0.15 g of HOBt, and 0.23 g of DCC.

Yield: 0.73 g (75.6%).
m.p.: 134°–136° C.
Rf¹: 0.45.
$[\alpha]_D^{24}$ −21.0° (c=0.6, DMF).
Elemental analysis, for $C_{49}H_{66}N_8O_{10}S \cdot H_2O$: Calcd. C, 60.22; H, 7.02; N, 11.47; S, 3.28. Found C, 60.54; H, 7.12; N, 11.18; S, 3.02.

(III)

Preparation of

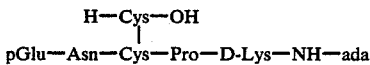

In the same manner as Example 2-(III), 0.70 g of pGlu—Asn—Cys(MBzl)—Pro—D—Lys(Z)—N-H—ada was treated with MSA-anisole, reacted with 94 mg of cystine monosulfoxide and purified on a Sephadex G-25 column to give the above-identified compound.

Yield: 300 mg (47%).
Rf⁴: 0.37.
$[\alpha]_D^{23}$ −111.5° (c=0.4, 1N-AcOH).
Amino acid analysis: Lys 1.00; Asp 0.98; Glu 1.08; Pro 1.03; Half Cys 1.63.

EXAMPLE 6

Production of

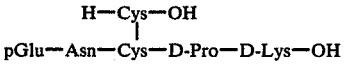

(I)

Preparation of Boc—Cys(MBzl)—D—Pro—OH

In a mixture of 90 ml of DMF and 10 ml of water was dissolved 5.76 g of D—Pro, followed by addition of 7 ml of TEA. With vigorous stirring, 21.9 of Boc—Cys(MBzl)—OSu was added. The mixture was stirred for 15 hours, at the end of which time it was concentrated. The concentrate was dissolved in 300 ml of AcOEt, washed with 0.5N-HCl and water in that order, dried over anhydrous sodium sulfate, and concentrated. The concentrate was applied to a silica gel column (250 g of silica gel), followed by elution with 5% MeOH-chloroform. The fractions rich in the desired compound were pooled and concentrated to give an oil.
Yield: 17.2 g (78.3%).
Rf¹: 0.71.

(II)

Preparation of Boc—Cys(MBzl)—D—Pro—D—Lys(Z)—OBzl

In 20 ml of DMF was dissolved 2.73 g of H—D—Lys(Z)—OBzl.p—Tos—OH and under ice-cooling, 0.71 ml of TEA was added, followed by addition of 2.20 g of Boc—Cys(MBzl)—D—Pro—OH, 0.99 g of HONB and 1.04 g of DCC. The mixture was stirred for 15 hours.

Then, DCU was filtered off, the filtrate was concentrated, and the residue was dissolved in 200 ml of AcOEt. The solution was washed with 0.5N-HCl and aqueous NaHCO₃ and water in that order, dried over anhydrous sodium sulfate, and concentrated. The concentrate was applied to a silica gel column (80 g of silica gel) and elution was carried out with 1.5% MeOH-chloroform. The fractions rich in the desired compound were combined and concentrated to give an oil.
Yield: 3.22 g (81.1%).
Rf²: 0.56.

(III)

Preparation of Boc—Asn—Cys(MBzl)—D—Pro—D—Lys(Z)—oBzl

To 3.07 g of Boc—Cys(MBzl)—D—Pro—D—Lys(Z)—oBzl was added 30 ml of TFA-water (19:1) and the mixture was shaken at room temperature for 30 minutes and concentrated. To the concentrate was added ether and the resulting precipitate was collected by filtration and dried. The precipitate was dissolved in 30 ml of DMF and under ice-cooling, 0.65 ml of TEA was added, followed by addition of Boc—Asn—ONB (prepared using 1.0 g of Boc—Asn—OH, 0.84 g of HONB and 0.89 g of DCC). The mixture was stirred for 15 hours, at the end of which time it was concentrated. The residue was dissolved in 200 ml of AcOEt, washed with 0.5N-HCl, aqueous NaHCO₃ and water in that order, dried over anhydrous sodium sulfate and concentrated. The concentrate was applied to a silica gel column (80 g silica gel) and elution was carried out with 2% MeOH-chloroform. The fractions rich in the desired compound were combined and concentrated to give an oil.
Yield: 2.45 g (69.7%).
Rf²: 0.34.

(IV)

Preparation of pGlu—Asn—Cys(MBzl)—D—Pro—D—Lys(Z)—OBzl

To 2.31 g of Boc—Asn—Cys(MBzl)—D—Pro—D—Lys(Z)—OBzl was added 20 ml of TFA-water (19:1). Then, in the same manner as Example 6-(III), the Boc group was removed and the resulting amine component was dissolved in 20 ml of DMF, followed by addition of pGlu—ONB (prepared by using 0.33 g of pGlu—OH, 0.50 g of HONB and 0.53 g of DCC) and 15-hour stirring. The reaction mixture was then treated in the same manner as Example 6-(III). Thus it was applied to a silica gel column (70 g of silica gel), followed by elution with 5% MeOH and then with 10% of MeOH-chloroform. The fractions rich in the desired compound were combined and concentrated. To the concentrate was added ether and the resulting precipitate was collected by filtration.
Yield: 1.51 g (64.6%).
m.p.: 69°–73° C.
Rf¹: 0.39.
[α]_D²³ +1.2° (c=1.0, MeOH).
Elemental analysis, for C₄₆H₅₇N₇O₁₁S.3/2H₂O: Calcd. C, 58.58; H, 6.41; N, 10.40; S, 3.40. Found C, 58.65; H, 6.35; N, 10.44; S, 3.54.

(V)

Preparation of

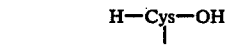

In the same manner as Example 2-(III), 1.34 of pGlu—Asn—Cys(MBzl)—D—Pro—D—Lys(Z)—OBzl was treated with MSA-anisole, reacted with 183 mg of cystine monosulfoxide, and purified on a Sephadex G-25 column to give the above-identified compound.
Yield: 0.61 g (59.7%).
Rf⁴: 0.12.
[α]_D²³ −88.1° (c=0.7, 1N-AcOH).
Amino acid analysis: Lys 1.00; Asp 0.95; Glu 1.08; Pro 1.05; Half Cys 1.70.

EXAMPLE 7

Production of

(I)

Preparation of Boc—Gly—D—Lys(Z)—OBzl

In the same manner as Example 1-(V), 3.0 g of Boc—D—Lys(Z)—OBzl was treated with TFA and the resulting amine component and Boc—Gly—ONB (prepared by using 1.12 g of Boc—Gly—OH, 1.27 g of HONB and 1.44 g of DCC) were stirred in 30 ml of acetonitrile for 15 hours. The unreacted Boc—Gly—ONB was decomposed with 0.5 ml of (CH₃)₂NH(CH₂)₃NH₂, followed by concentration. The residue was dissolved in 100 ml of AcOEt, washed with aqueous NaHCO₃, 10% aqueous citric acid and water, and dried over anhydrous sodium sulfate. It was then concentrated to give an oil.
Yield: 3.2 g (95.1%).
Rf¹: 0.77.

(II)

Preparation of Boc—Cys(MBzl)—Gly—D—Lys(Z)—OBzl

In 20 ml of TFA was dissolved 3.1 g of Boc—Gly—D—Lys(Z)—OBzl with shaking and the solution was concentrated. Then 3.5 ml of 2N-HCl-dioxane, followed by addition of ether and petroleum ether, whereupon an oily substance separated out. The solvent was removed by decantation. The oily substance was dissolved in 30 ml of acetonitrile and after neutralization with TEA, Boc—Cys(MBzl)—ONB (prepared by using 2.05 g of Boc—Cys(MBzl)—OH, 1.20 g of HONB and 1.40 g of DCC) was added. The mixture was stirred for 15 hours, after which it was concentrated and dissolved in 100 ml of AcOEt. The solution was washed with aqueous NaHCO₃, 10% aqueous citric acid and water in that order, dried over anhydrous sodium sulfate, and concentrated. To the residue was added ether and the resulting crystals were collected by filtration.

Yield: 3.65 g (81.0%).
m.p.: 106°–107° C.
$Rf^1$: 0.71.
$[\alpha]_D^{24} +6.9°$ (c=1.1, MeOH).
Elemental analysis, for $C_{39}H_{50}N_4O_9S$: Calcd. C, 62.38; H, 6.71; N, 7.46; S, 4.27. Found C, 62.55; H, 6.79; N, 7.54; S, 4.42.

(III)

Preparation of
Boc—Asn—Cys(MBzl)—Gly—D—Lys(Z)—OBzl

In 20 ml of TFA was dissolved 3.50 g of Boc—Cys(MBzl)—Gly—D—Lys(Z)—OBzl with shaking and the solution was concentrated. To the concentrate was added ether and the resulting precipitate was collected by filtration. The precipitate was dissolved in 10 ml of DMF and under ice-cooling, 1 ml of TEA was added. Then, Boc—Asn—ONB (prepared by using 1.63 g of Boc—Asn—OH, 1.39 g of HONB and 1.59 g of DCC) was added and the mixture was stirred for 15 hours. The reaction mixture was concentrated, the residue was dissolved in AcOEt, and the solution was washed with aqueous NaHCO₃ and aqueous citric acid, dried over anhydrous sodium sulfate, and concentrated. To the residue was added ether and the resulting precipitate was collected by filtration.

Yield: 4.0 g (99.2%).
m.p.: 124°–125° C.
$Rf^1$: 0.63.
$[\alpha]_D^{24} -13.6°$ (c=0.9, MeOH).
Elemental analysis, for $C_{43}H_{56}N_6O_{11}S$: Calcd. C, 59.71; H, 6.53; N, 9.72; S, 3.71. Found C, 59.86; H, 6.65; N, 9.76; S, 3.45.

(IV)

Preparation of
pGlu—Asn—Cys(MBzl)—Gly-D-Lys(Z)—OBzl

In the same manner as Example 7-(III), 0.70 g of Boc—Asn—Cys(MBzl)—Gly—D—Lys(Z)—OBzl was treated with TFA and the resulting amine component was dissolved in 5 ml of DMF. Under ice-cooling, 0.2 ml of TEA and 0.26 g of pGlu-ONB were added and the mixture was stirred for 15 hours. The reaction mixture was concentrated. To the concentrate was added acetonitrile-AcOEt and the resulting precipitate was collected by filtration.

Yield: 0.58 g (81.7%).
m.p.: 170°–174° C.
$Rf^1$: 0.30.
$[\alpha]_D^{24} -15.1°$ (c=1.1, DMF).
Elemental analysis, for $C_{43}H_{53}N_7O_{11}S\cdot H_2O$: Calcd. C, 57.77; H, 6.20; N, 10.97; S, 3.59. Found C, 58.05; H, 6.10; N, 11.02; S, 3.47.

(V)

Preparation of

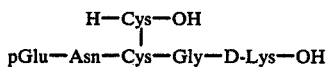

In the same manner as in Example 2-(III), 0.40 g of pGlu-Asn-Cys (MBzl)-Gly-D-Lys(Z)-OBzl was treated with MSA-anisole, reacted with 60 mg of cystine monosulfoxide, and purified on a Sephadex G-25 column to give the above-identified compound.

Yield: 155 mg (52%).
$Rf^4$: 0.09.
$[\alpha]_D^{23} -122.8°$ (c=0.6, 1N-AcOH).
Amino acid analysis: Lys 1.00; Asp 1.07; Glu 1.10; Gly 1.07; Half Cys 1.66.

EXAMPLE 8

Production of

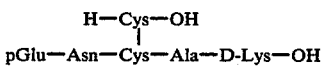

(I)

Preparation of Boc—Ala—D—Lys(Z)—OBzl

Using 3.00 g of Boc—D—Lys(Z)—OBzl, 1.21 g of Boc—Ala—OH, 1.27 g of HONB and 1.44 g of DCC, the procedure of Example 7-(I) was repeated to give the desired compound, which was crystalized from ether and recovered by filtration.

Yield: 2.90 g (83.9%).
m.p.: 105°–107° C.
$Rf^1$: 0.68.
$[\alpha]_D^{24} -1.2°$ (c=1.0, MeOH).
Elemental analysis, for $C_{29}H_{39}N_3O_7$: Calcd. C, 64.31; H, 7.26; N, 7.76. Found C, 64.54; H, 7.31; N, 7.83.

(II)

Preparation of
Boc—Cys(MBzl)—Ala—D—Lys(Z)—OBzl

Using 2.70 g of Boc—Ala—D—Lys(Z)—OBzl, 1.71 g of Boc—Cys(MBzl)—OH, 1.00 g of HONB and 1.13 g of DCC, the procedure of Example 7-(II) was repeated to give the desired compound, which was precipitated by addition of ether and collected by filtration.

Yield: 3.60 g (94.1%).
m.p.: 114°–115° C.
$Rf^1$: 0.72.
$[\alpha]_D^{24} +5.9°$ (c=1.2, MeOH).
Elemental analysis, for $C_{40}H_{52}N_4O_9S$: Calcd. C, 62.81; H, 6.85; N, 7.32; S, 4.19. Found C, 62.97; H, 6.89; N, 7.40; S, 4.06.

(III)

Preparation of
Boc—Asn—Cys(MBzl)—Ala—D—Lys(Z)—OBzl

Using 3.40 g of Boc—Cys(MBzl)—Ala—D—Lys(Z)—OBzl, 1.55 g of Boc—Asn—OH, 1.32 g of HONB and 1.51 g of DCC, the procedure of Example 7-(III) was repeated to give the desired compound.

Yield: 3.90 g (quantitative).
m.p.: 142°–143° C.
$Rf^1$: 0.61.

$[\alpha]_D^{24}$ −9.6° (c=1.2, MeOH).

Elemental analysis, for $C_{44}H_{58}N_6O_{11}S$: Calcd. C, 60.12; H, 6.65; N, 9.56; S, 3.65. Found C, 60.26; H, 6.87; N, 9.69; S, 3.49.

(IV)

Preparation of pGlu—Asn—Cys(MBzl)—Ala—D—Lys(Z)—OBzl

Using 0.70 g of Boc—Asn—Cys(MBzl)—Ala—D—Lys(Z)—OBzl and 0.26 g of pGlu—ONB, the procedure of Example 7-(IV) was repeated to give the desired compound, which was precipitated from AcOEt-ether and the precipitate was collected by filtration.

Yield: 0.61 g (85.7%).
m.p.: 197°–200° C.
$Rf^1$: 0.35.
$[\alpha]_D^{24}$ =9.6° (c=1.0, DMF).

Elemental analysis, for $C_{44}H_{55}N_{11}O_7S \cdot \frac{1}{2}H_2O$: Calcd. C, 58.78; H, 6.28; N, 10.91; S, 3.57. Found C, 58.73; H, 6.18; N, 11.02; S, 3.89.

(V)

Preparation of

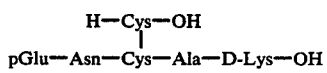

In the same manner as Example 2-(III), 0.40 g of pGlu—Asn—Cys(MBzl)—Ala—D—Lys(Z)—OBzl was treated with MSA-anisole, reacted with 60 mg of cystine monosulfoxide, and purified on a Sephadex G-25 column to give the desired compound.

Yield: 247 mg (82.6%).
$Rf^4$: 0.10.
$[\alpha]_D^{23}$ −122.6° (c=0.4, 1N-AcOH).

Amino acid analysis: Lys 1.00; Asp 1.09; Glu 1.11; Ala 1.04; Half Cys 1.81.

EXAMPLE 9

Production of

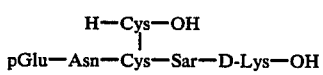

(I)

Preparation of Boc—Sar—D—Lys(Z)—OBzl

Using 3.00 g of Boc—D—Lys(Z)—OBzl, 1.25 g of Boc—Sar—OH, 1.27 g of HONB and 1.44 g of DCC, the procedure of Example 7-(I) was repeated to give the desired compound as an oil.

Yield: 3.5 g (quantitative).
$Rf^1$: 0.72.

(II)

Preparation of Boc—Cys(MBzl)—Sar—D—Lys(z)—OBzl

Using 3.3 g of Boc—Sar—D—Lys(Z)—OBzl, 2.05 g of Boc—Cys(MBzl)—OH, 1.20 g of HONB and 1.40 g of DCC, the procedure of Example 7-(II) was repeated to give the desired compound, which was precipitated from ether and the preceipate was collected by filtration.

Yield: 4.10 g (89.3%).

m.p.: 93°–94° C.
$Rf^1$: 0.74.
$[\alpha]_D^{24}$ +6.5° (c=1.0, MeOH).

Elemental analysis, for $C_{40}H_{52}N_4O_9S$: Calcd. C, 62.81; H, 6.85; N, 7.32; S, 4.19. Found C, 63.04; H, 6.84; N, 7.39; S, 4.07.

(III)

Preparation of Boc—Asn—Cys(MBzl)—Sar—D—Lys(Z)—OBzl

Using 3.90 g of Boc—Cys(MBzl)—Sar—D—Lys(Z)—OBzl, 1.78 g of Boc—Asn—OH, 1.51 g of HONB and 1.74 g of DCC, the procedure of Example 7-(III) was repeated to give the desired compound, which was precipitated from ether and the preceipate was collected by filtration.

Yield: 4.30 g (95.9%).
m.p.: 104°–106° C.
$Rf^1$: 0.61.
$[\alpha]_D^{24}$ −11.0° (c=1.0, MeOH).

Elemental analysis, for $C_{44}H_{58}N_6O_{11}S$: Calcd. C, 60.12; H, 6.65; N, 9.56; S, 3.65. Found C, 60.34; H, 6.84; N, 9.64; S, 3.51.

(IV)

Preparation of pGlu—Asn—Cys(MBzl)—Sar—D—Lys(Z)—OBzl

Using 0.70 g of Boc—Asn—Cys(MBzl)—Sar—D—Lys(Z)—OBzl and 0.26 g of pGlu—ONB, the procedure of Example 7-(IV) was repeated to give the desired compound.

Yield: 0.58 g (81.5%).
m.p.: 167°–172° C.
$Rf^1$: 0.34.
$[\alpha]_D^{24}$ −10.5° (c=1.0, DMF).

Elemental analysis, for $C_{44}H_{57}N_7O_{11}S \cdot \frac{1}{2}H_2O$: Calcd. C, 58.78; H, 6.28; N, 10.91; S, 3.57. Found C, 58.84; H, 6.26; N, 10.97; S, 3.25.

(V)

Preparation of

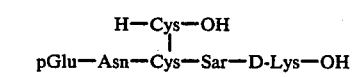

In the same manner as Example 2-(III), 0.40 g of pGlu—Asn—Cys(MBzl)—Sar—D—Lys(Z)—OBzl was treated with MSA-anisole, reacted with 60 mg of cystine monosulfoxide, and purified on a Sephadex G-25 column to give the desired compound.

Yield: 216 mg (72.2%).
$Rf^4$: 0.08.
$[\alpha]_D^{23}$ −111.6° (c=0.5, 1N-AcOH).

Amino acid analysis: Lys 1.00; Asp 1.01; Glu 1.09; Sar 1.00; Half Cys 1.65.

EXAMPLE 10

Production of

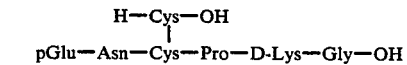

(I) CL Preparation of Boc—D—Lys(Z)—Gly—OBzl

In 15 ml of acetonitrile was dissolved 1.44 g of H—Gly—OBzl.p—Tos—OH and under ice-cooling, 0.6 ml of TEA was added. To this was added Boc—D—Lys(Z)—ONB (prepared using 2.00 g of Boc—D—Lys(Z)—OH.DCHA, 0.17 g of HONB, and 0.81 g of DCC) and the mixture was stirred for 15 hours. The reaction mixture was concentrated and the residue was dissolved in AcOEt, washed with aqueous NaHCO3 and 10% aqueous citric acid, dried over anhydrous sodium sulfate, and concentrated. To the residue was added ether-petroleum ether and the resulting crystals were collected by filtration.

Yield: 1.90 g (quantitative).
m.p.: 62°–63° C.
$Rf^1$: 0.75.
$[\alpha]_D^{24}+13.2°$ (c=1.0, MeOH).
Elemental analysis, for $C_{28}H_{37}N_3O_7$: Calcd. C, 63.74; H, 7.07; N, 7.96. Found C, 63.88; H, 7.13; N, 8.12.

(II)

Preparation of
pGlu—Asn—Cys(MBzl)—Pro—D—Lys(Z)—Gly—OBzl

Using 1.03 g of Boc—D—Lys(Z)—Gly—OBzl, 1.0 g of pGlu—Asn—Cys(MBzl)—Pro—OH, 0.36 g of HONB and 0.41 g of DCC, the procedure of Example 2-(II) was repeated to give the desired compound.
Yield: 1.14 g (66.2%).
m.p.: 168°–171° C.
$Rf^1$: 0.40.
$[\alpha]_D^{24}-9.7°$ (c=0.9, DMF).
Elemental analysis, for $C_{48}H_{60}N_8O_{12}S$: Calcd. C, 59.25; H, 6.21; N, 11.51; S, 3.30. Found C, 59.52; H, 6.34; N, 11.32; S, 3.13.

(III)

Preparation of

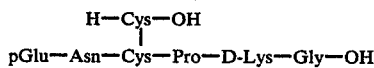
pGlu—Asn—Cys—Pro—D-Lys—Gly—OH

In the same manner as Example 2-(III), 0.80 g of pGlu—Asn—Cys(MBzl)—Pro—D—Lys(Z)—Gly—OBzl was treated with MSA-anisole, reacted with 116 mg of cystine monosulfoxide, and purified on a Sephadex G-25 column to give the desired compound.
Yield: 475 mg (77%).
$Rf^4$: 0.08.
$[\alpha]_D^{23}-136.9°$ (c=0.5, 1N-AcOH).
Amino acid analysis: Lys 1.00; Asp 1.01; Glu 1.10; Pro 1.03; Ala 0.95; Half Cys 1.62.

EXAMPLE 11

Production of

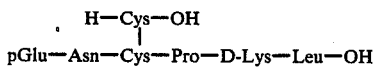
pGlu—Asn—Cys—Pro—D-Lys—Leu—OH (I) CL Preparation of Boc—D—Lys(Z)—Leu—OBzl Using 1.68 g of H—Leu—OBzl.p—Tos—OH, 2.0 g of Boc—D—Lys(Z)—OH.DCHA, 0.71 g of HONB and 0.81 g of DCC, the procedure of Example 10-(I) was repeated to give the desired compound.
Yield: 2.0 g (96.2%).
m.p.: 66°–69° C.
$Rf^1$: 0.80.
$[\alpha]_D^{24}+2.0°$ (c=1.1, MeOH).
Elemental analysis, for $C_{32}H_{45}N_3O_7$: Calcd. C, 65.84; H, 7.77; N, 7.20.
Found C, 65.81; H, 7.74; N, 7.33.

(II)

Preparation of
pGlu—Asn—Cys(MBzl)—Pro—D—Lys(Z)—Leu—OBzl

Using 1.14 g of Boc—D—Lys(Z)—Leu—OBzl, 1.0 g of pGlu—Asn—Cys(MBzl)—Pro—OH, 0.36 g of HONB and 0.41 g of DCC, the procedure of Example 2-(II) was repeated to give the desired compound.
Yield: 1.24 g (68.1%).
m.p.: 165°–168° C.
$Rf^1$: 0.46.
$[\alpha]_D^{24}-24.4°$ (c=1.1, DMF).
Elemental analysis, for $C_{52}H_{68}N_8O_{12}S$: Calcd. C, 60.68; H, 6.66; N, 10.89; S, 3.12. Found C, 60.82; H, 6.80; N, 10.74; S, 2.96.

(III)

Preparation of

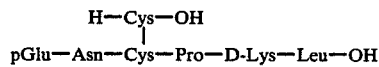
pGlu—Asn—Cys—Pro—D-Lys—Leu—OH

In the same manner as Example 2-(III), 0.80 g of pGlu—Asn—Cys(MBzl)—Pro—D—Lys(Z)—Leu—OBzl was treated with MSA-anisole, reacted with 100 mg of cystine monosulfoxide, and purified on a Sephadex G-25 column to give the desired compound.
Yield: 300 mg (48%).
$Rf^4$: 0.19.
$[\alpha]_D^{23}-131.3°$ (c=0.7, 1N-AcOH).
Amino acid analysis: Lys 1.00; Asp 0.93; Glu 1.04; Pro 1.03; Leu 0.96; Half Cys 1.75.

EXAMPLE 12

Production of

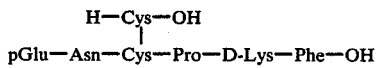
pGlu—Asn—Cys—Pro—D-Lys—Phe—OH (I) CL Preparation of Boc—D—Lys(Z)—Phe—OBzl Using 1.83 g of H—Phe—OBzl.p—Tos—OH, 2.0 g of Boc—D—Lys(Z)—OH.DCHA, 0.71 g of HONB and 0.81 g of DCC, the procedure of Example 10-(I) was repeated to give the desired compound.
Yield: 2.15 g (97.8%).
m.p.: 137°–138° C.
$Rf^1$: 0.83.
$[\alpha]_D^{24}-2.9°$ (c=0.8, MeOH).
Elemental analysis, for $C_{35}H_{43}N_3O_7$: Calcd. C, 68.05; H, 7.02; N, 6.80. Found C, 60.09; H, 7.13; N, 6.91.

(II)

Preparation of
pGlu—Asn—Cys(MBzl)—Pro—D—Lys(Z)—
Phe—OBzl

Using 1.20 g of Boc—D—Lys(Z)—Phe—OBzl, 1.0 g of pGlu—Asn—Cys(MBzl)—Pro—OH, 0.36 g of HONB and 0.41 g of DCC, the procedure of Example 2-(II) was repeated to give the desired compound.
Yield: 1.08 g (56.6%).
m.p.: 168°–173° C.
Rf$^1$: 0.50.
$[\alpha]_D^{24}$ −20.0° (c=0.9, DMF).
Elemental analysis, for $C_{55}H_{66}N_8O_{12}S$: Calcd. C, 62.13; H, 6.26; N, 10.54; S, 3.02. Found C, 62.58; H, 6.63; N, 10.51; S, 2.48.

(III)

Preparation of

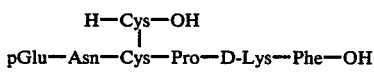

In the same manner as Example 2-(III), 0.80 g of pGlu—Asn—Cys(MBzl)—Pro—D—Lys(Z)—
Phe—OBzl was treated with MSA-anisole, reacted with 96 mg of cystine monosulfoxide, and purified on a Sephadex G-25 column to give the desired compound.
Yield: 345 mg (55%).
Rf$^4$: 0.19.
$[\alpha]_D^{23}$ −123.9° (c=0.4, 1N-AcOH).
Amino acid analysis: Lys 1.00; Asp 0.98; Glu 1.05; Pro 1.01; Phe 0.95; Half Cys 1.63.

EXAMPLE 13

Production of

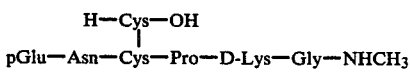

(I)

Preparation of Boc—D—Lys(Z)—Gly—NHCH$_3$

Using H—Gly—NHCH$_3$ (prepared by catalytic reduction of 1.50 g of Z—Gly—NH—CH$_3$), 3.77 g of Boc—D—Lys(Z)—OH.DCHA, 1.32 g of HONB and 1.39 g of DCC, the procedure of Example 10-(I) was repeated to give the desired compound as an oil.
Yield: 2.20 g (71.8%).
Rf$^2$: 0.25.

(II)

Preparation of
pGlu—Asn—Cys(MBzl)—Pro—D—Lys(Z)—
Gly—NHCH$_3$

Using 1.37 g of Boc—D—Lys(Z)—Gly—NH—CH$_3$, 1.69 g of pGlu—Asn—Cys(MBzl)—Pro—OH, 1.07 g of HONB and 0.93 g of DCC, the procedure of Example 2-(II) was repeated to give the desired compound, which was reprecipitated from methanol-acetonitrile.
Yield: 1.67 g (62.2%).
m.p.: 169°–172° C.
Rf$^3$: 0.27.
$[\alpha]_D^{24}$ −48.5° (c=0.9, MeOH).

Elemental analysis, for $C_{42}H_{57}N_9O_{11}S.2H_2O$: Calcd. C, 54.12; H, 6.60; N, 13.53; S, 3.44. Found C, 54.33; H, 6.34; N, 13.53; S, 3.38.

(III)

Preparation of

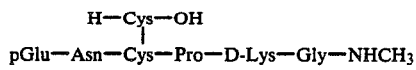

In the same manner as Example 2-(III), 1.53 g of pGlu—Asn—Cys(MBzl)—Pro—D—Lys(Z)—
Gly—NHCH$_3$ was treated with MSA-anisole, reacted with 175 mg of cystine monosulfoxide, and purified on a Sephadex G-25 column to give the desired compound.
Yield: 801 mg (57%).
Rf$^4$: 0.14.
$[\alpha]_D^{24}$ −130.0° (c=0.7, 1N-AcOH).
Amino acid analysis: Lys 1.00; Asp 1.02; Glu 1.09; Pro 1.03; Gly 0.96; Half Cys 1.71; CH$_3$NH$_2$ 0.93.

EXAMPLE 14

Production of

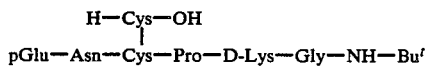

(I)

Preparation of Boc—D—Lys(Z)—Gly—NH—Bu$^t$

Using H—Gly—NH—Bu$^t$ (prepared by catalytic reduction of 1.75 g of Z—Gly—NH—Bu$^t$), 3.71 g of Boc—D—Lys(Z)—OH.DCHA, 1.30 g of HONB and 1.37 g of DCC, the procedure of Example 10-(I) was repeated to give the desired compound as an oil.
Yield: 2.75 g (84.5%).
Rf$^2$: 0.29.

(II)

Preparation of
pGlu—Asn—Cys(MBzl)—Pro—D—Lys(Z)—
Gly—NH—Bu$^t$

Using 1.48 g of Boc—D—Lys(Z)—Gly—NH—Bu$^t$, 1.69 g of pGlu—Asn—Cys(MBzl)—Pro—OH, 1.07 g of HONB and 0.93 g of DDC, the procedure of Example 2-(II) was repeated to give the desired compound, which was reprecipitated from methanol-acetonitrile-AcOEt.
Yield: 1.08 g (38.4%)
m.p.: 115°–120° C.
Rf$^3$: 0.38.
$[\alpha]_D^{24}$ −44.3° (c=0.5, MeOH).
Elemental analysis, for $C_{45}H_{63}N_9O_{11}S.3H_2O$: Calcd. C, 54.48; H, 7.01; N, 12.71; S, 3.23. Found C, 54.23; H, 6.39; N, 12.58; S, 3.15.

(III)

Preparation of

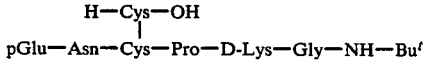

In the same manner as Example 2-(III), 0.99 g of pGlu—Asn—Cys(MBzl)—Pro—D—Lys(Z)—
Gly—NH—Bu$^t$ was treated with MSA-anisole, reacted with 115 mg of cystine monosulfoxide, and purified on a Sephadex G-25 column to give the desired compound.

Yield: 525 mg (58%).

Rf⁴: 0.20.

$[\alpha]_D^{23}$ −123.3° (c=0.6, 1N-AcOH).

Amino acid analysis: Lys 1.00; Asp 0.98; Glu 1.05; Pro 1.00; Gly 0.97; Half Cys 1.70.

EXAMPLE 15

Production of

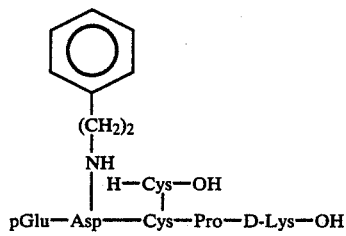

(I)

Preparation of

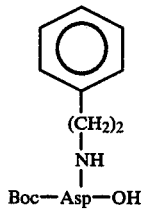

In 10 ml of acetonitrile were dissolved 3.23 g of Boc—Asp—oBzl and 1.38 ml of benzylamine and the solution was ice-cooled. To this was added 2.27 g of DCC and the mixture was stirred at room temperature for 5 hours. The resulting precipitate was filtered off, the filtrate was concentrated, and the residue was dissolved in 10 ml of AcOEt. The solution was then washed with 10% aqueous citric acid, a saturated aqueous solution of NaHCO₃ and water in that order, dried over anhydrous sodium sulfate, and concentrated. The resulting oil was dissolved in 10 ml of methanol and subjected to catalytic reduction with palladium black as the catalyst. Following this reaction, the catalyst was filtered off and the filtrate was distilled off to give crude crystals, which were recrystallized from EtOAC/Et₂O.

Yield: 2.43 g (72.2%).

m.p.: 118°–120° C.

Rf¹: 0.80.

$[\alpha]_D^{23}$ +2.9° (c=0.3, MeOH).

Elemental analysis, for C₁₇H₂₄N₂O₅: Calcd. C, 60.70; H, 7.19; N, 8.33. Found C, 60.60; H, 7.18; N, 8.42.

(II)

Preparation of

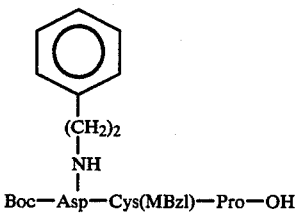

In 5 ml of DMF was dissolved 270 mg of

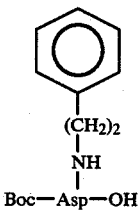

and the solution was ice-cooled. Then, 179 mg of HONB and 165 mg of DCC were added thereto, and the mixture was stirred at room temperature for 4 hours. Separately, 2 ml of TFA-water (19:1) was added to 438 mg of Boc—Cys(MBzl)—Pro—OH and after shaking at room temperature for 30 minutes, the mixture was concentrated. To this was added ether, and the resulting precipitate was collected by filtration and dried. This preparation was added to the above-prepared solution and after ice-cooling, 0.28 ml of TEA was added. The mixture was stirred at room temperature for 15 hours. Following this reaction, the precipitate was filtered off and the filtrate was concentrated. The residue was dissolved in 10 ml of AcOEt, washed with 10% aqueous citric acid and water in that order, dried over anhydrous sodium sulfate, and concetrated to give an oil.

Yield: 487 mg (92.7%).

Rf¹: 0.79.

(III)

Preparation of

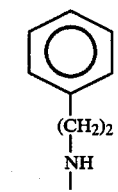

To 459 mg of

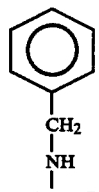

Boc—Asp—Cys(MBzl)—Pro—OH was added 2 ml of TFA-water (19:1) and the mixture was shaken at room temperature for 30 minutes and concentrated. To the concentrate was added either and the resulting precipitate was collected by filtration and dried. The precipitate was dissolved in 5 ml of DMF, followed by addition of 203 mg of pGlu—ONB and 0.20 ml of TEA. The mixture was stirred at room temperature for 15 hours. The solution was concentrated and the residue was dissolved in 10 ml of AcOEt, washed with 10% aqueous citric acid and water in that order and dried over anhydrous sodium sulfate. Finally, the solvent was distilled off to give an oil.

Yield: 455 mg (97.3%).
Rf$^1$: 0.31.

(IV)

Preparation of

pGlu—Asp—Cys(MBzl)—Pro—D-Lys(Z)—OBu$^t$

In 10 ml of DMF were dissolved 434 mg of

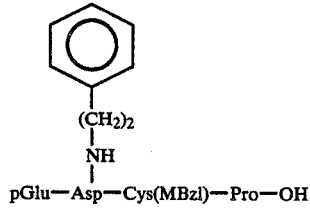

pGlu—Asp—Cys(MBzl)—Pro—OH and 219 mg of H—D—Lys(Z)—OBu$^t$. The solution was ice-cooled and 88 mg of HOBt and 134 mg of DCC were added. The mixture was stirred at room temperature for 15 hours. The resulting precipitate was filtered off and the filtrate was concentrated. To the concentrate was added CH$_3$CN, the insoluble matter was filtrated off again, and the filtrate was further concentrated and precipitated with Et$_2$O. The precipitate was collected by filtration and dried.

Yield: 0.41 g (64.0%).
m.p.: 120°–123° C.
[α]$_D^{23}$ −30.3° (c=0.4, DMF).
Rf$^5$: 0.40.

Elemental analysis, for C$_{51}$H$_{67}$N$_7$O$_{11}$S: Calcd. C, 62.11; H, 6.85; N, 9.94; S, 3.25. Found C, 62.31; H, 6.77; N, 9.38; S, 3.32.

(V)

Preparation of

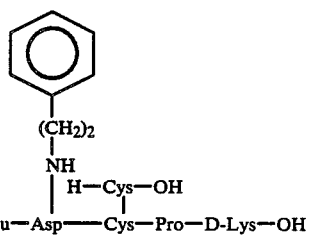

pGlu—Asp—Cys—Pro—D-Lys—OH

In the same manner as Example 2-(III), 0.36 g of

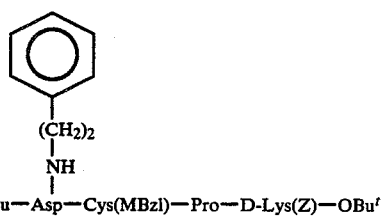

pGlu—Asp—Cys(MBzl)—Pro—D-Lys(Z)—OBu$^t$ was treated with MSA-anisole, reacted with 46 mg of cystine monosulfoxide, and purified on a Sephadex G-25 column to give the above-identified compound.

Yield: 183 mg (75.3%).
Rf$^4$: 0.33.
[α]$_D^{23}$ −131.1° (c32 0.4, H$_2$O).

Amino acid analysis: Lys 1.00; Asp 0.97; Glu 1.04; Pro 0.98; Half Cys 1.67.

EXAMPLE 16

Production of

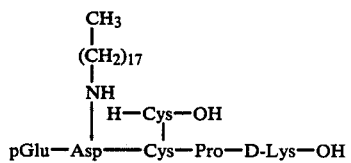

pGlu—Asp—Cys—Pro—D-Lys—OH (I)

Preparation of

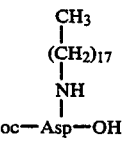

Boc—Asp—OH

In 10 ml of acetonitrile were dissolved 3.23 g of Boc—Asp—oBzl and 2.70 g of stearylamine and after ice-cooling, 2.27 g of DCC was added. The mixtures was stirred at room temperature for 5 hours. The precipitate formed was filtered off, the filtrate was concentrated, and the residue was directly dissolved in 30 ml of tetrahydrofuran and subjected to catalytic reduction with palladium black as the catalyst. After the reaction, the catalyst was filtered off and the filtrate was distilled to give a solid precipitate. This precipitate was recrystallized from methanol.

Yield: 1.40 g (28.9%).

m.p.: 100°–103° C.
Rf¹: 0.76.
$[\alpha]_D^{23}+1.1°$ (c=0.3, MeOH).
Elemental analysis, for $C_{27}H_{52}N_2O_5$: Calcd. C, 66.90; H, 10.81; N, 5.78. Found C, 66.84; H, 10.93; N, 5.61.

(II)

Preparation of

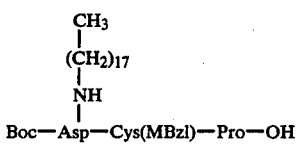

In 30 ml of tetrahydrofuran was dissolved 0.97 g of

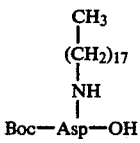

and after ice-cooling, 0.36 g of HONB and 0.42 g of DCC were added. The mixture was stirred at room temperature for 4 hours. Separately, 3 ml of TFA-water (19:1) was added to 0.88 g of Boc—Cys(MBzl)—Pro—OH and the mixture was shaken at room temperature for 30 minutes and concentrated. To the concentrate was added ether and the resulting precipitate was collected by filtration and dried. This preparation was added to the above solution and after ice-cooling, 0.56 ml of TEA was added. The mixture was stirred at room temperature for 15 hours. Thereafter, the same procedure as Example 15-(II) was repeated to give the above-identified compound.
Yield: 1.35 g (82.9%).
Rf¹: 0.76.

(III)

Preparation of

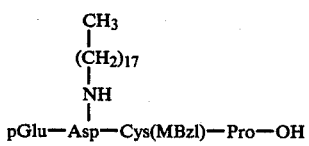

To 1.21 g of

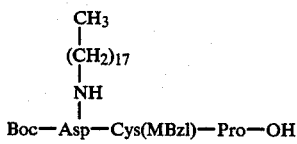

was added 10 ml of TFA-water (19:1) and the mixture was shaken at room temperature for 30 minutes and concentrated. To the concentrate was added ether-petroleum ether and the solvent was decanted off. The residue was allowed to stand in vacuo overnight. It was then dissolved in 10 ml of DMF, followed by addition of 0.44 g of pGlu-ONB and 0.42 ml of TEA, and mixture was stirred at room temperature for 15 hours. The solution was concentrated, followed by addition of 10 ml of acetonitrile, and the solid precipitate was collected by filtration.
Yield: 0.53 g (64.9%).
Rf¹: 0.28.

(IV)

Preparation of

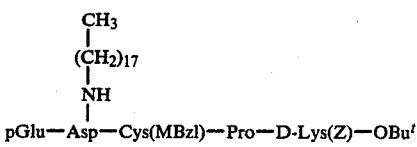

In 10 ml of DMF were dissolved 0.2 g of H—D—Lys(Z)—OBu$^t$ and 0.49 g of

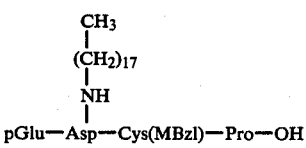

and the solution was ice-cooled. Then, 81 mg of HOBt and 124 mg of DCC were added thereto and the mixture was stirred at room temperature for 15 hours. Thereafter, the procedure of Example 15-(IV) was repeated to give the above-identified compound.
Yield: 0.36 g (52.9%).
m.p.: 95°–105° C.
$[\alpha]_D^{23}-21.1°$ (c=0.3, DMF).
Rf⁵: 0.37.
Elemental analysis, for $C_{61}H_{95}N_7O_{11}S$: Calcd. C, 64.58; H, 8.44; N, 8.64; S, 2.83. Found C, 64.39; H, 8.57; N, 8.92; S, 2.71.

(V)

Preparation of

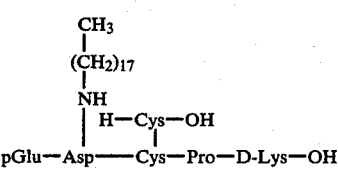

In the same manner as Example 2-(III), 275 mg of

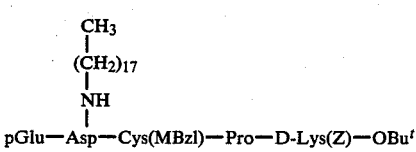

was treated with MSA-anisole, reacted with 31 mg cystine monosulfoxide, and purified on a Sephadex G-25 column to give the above-identified compound.
Yield: 180 mg (76.7%).
Rf⁴: 0.52.
$[\alpha]_D^{23}-80.5°$ (c=0.4, H₂0).
Amino acid analysis: Lys 1.00; Asp 1.02; Glu 0.96; Pro 0.96; Half Cys 1.59.

What is claimed is:
1. A peptide derivative of the general formula

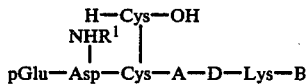

wherein
- $R^1$ is a hydrogen atom, a $C_{1-18}$ alkyl group or an unsubstituted phenyl $C_{1-3}$ alkyl group or a phenyl $C_{1-3}$ alkyl group in which the phenyl is substituted by nitro, halogen or alkoxy;
- A is an amino or N-$C_{1-6}$ alkylamino acid residue;
- B is a hydroxyl group, an amino group or an amino group substituted by alkyl, or an amino acid or an amide thereof, or a physiologically acceptable salt thereof.

2. The peptide derivative according to claim 1, wherein $R^1$ is a hydrogen atom.

3. The peptide derivative according to claim 1, wherein A is an amino or N—$C_{1-6}$ alkylamino acid residue represented by the formula

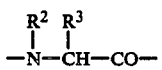

wherein $R^2$ and $R^3$ may be the same or different and each means a hydrogen atom or an unsubstituted $C_{1-6}$ alkyl group or a $C_{1-6}$ alkyl group substituted by an amino, carboxyl, carbamoyl or hydroxyl, or $R^2$ and $R^3$ may join together to form a ring of $(CH_2)_n$ (wherein n is an integer of 2 to 4).

4. The peptide derivative according to claim 1, wherein B is a hydroxyl group.

5. The peptide derivative according to claim 1, wherein B is a substituted or unsubstituted amino group represented by the formula

wherein $R^4$ is a hydrogen atom or a $C_{1-10}$ alkyl group.

6. The peptide derivative according to claim 1, wherein B is an amino acid or an amide thereof represented by the formula

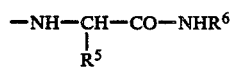

wherein
- $R^5$ is a hydrogen atom, a $C_{1-6}$ alkyl group or a phenyl $C_{1-3}$ alkyl group and
- $R^6$ is a hydrogen atom or a $C_{1-6}$ alkyl group.

7. The peptide derivative according to claim 1, wherein $R^1$ is a hydrogen atom, A is Pro and B is a hydroxyl group.

8. The peptide derivative according to claim 1, wherein $R^1$ is a hydrogen atom, A is D—Pro and B is a hydroxyl group.

9. The peptide derivative according to claim 1, wherein $R^1$ is a hydrogen atom, A is Ala and B is a hydroxyl group.

10. The peptide derivative according to claim 1, wherein $R^1$ is a phenylethyl group, A is Pro and B is a hydroxyl group.

11. A pharmaceutical composition for treating and/or preventing dementia which comprises, as an active ingredient, an effective amount of a compound or its salt as defined in claim 1, and a physiologically acceptable carrier or diluent therefor.

12. A method of treating and/or preventing dementia, which comprises administering an effective amount of a compound or its salt as defined in claim 1.

* * * * *